United States Patent
Wolgen et al.

(10) Patent No.: US 11,286,288 B2
(45) Date of Patent: *Mar. 29, 2022

(54) PHARMACEUTICAL COMPOUND

(71) Applicant: VALLAURIX PTE. LTD., Singapore (SG)

(72) Inventors: Philippe Wolgen, Singapore (SG); Roland Callens, Tielt (BE)

(73) Assignee: VALLAURIX PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/698,214

(22) Filed: Nov. 27, 2019

(65) Prior Publication Data

US 2020/0095303 A1 Mar. 26, 2020

Related U.S. Application Data

(62) Division of application No. 15/569,586, filed as application No. PCT/IB2016/052417 on Apr. 28, 2016, now Pat. No. 10,508,142.

(30) Foreign Application Priority Data

Apr. 28, 2015 (EP) .................................. 15165536

(51) Int. Cl.
*C07K 14/685* (2006.01)
*A61K 38/00* (2006.01)

(52) U.S. Cl.
CPC .......... *C07K 14/685* (2013.01); *A61K 38/00* (2013.01)

(58) Field of Classification Search
None
See application file for complete search history.

(56) References Cited

U.S. PATENT DOCUMENTS

| 2018/0086789 A1 | 3/2018 | Wolgen | |
| 2020/0246436 A1* | 8/2020 | Wolgen | ......... A61K 38/08 |

FOREIGN PATENT DOCUMENTS

| EP | 2487185 A1 | 8/2012 | |
| WO | WO 2006/012667 | 2/2006 | |
| WO | WO 2007/022774 A1 | 3/2007 | |
| WO | WO 2008/025094 | 3/2008 | |
| WO | WO 2012/107592 | 8/2012 | |
| WO | WO-2012107592 A1 * | 8/2012 | ............. A61P 35/00 |

OTHER PUBLICATIONS

Cydzik et al. "Derivatization of peptides as quaternary ammonium salts for sensitive detection by ESI-MS" J. Peptide Sci. 17:445-453. (Year: 2011).*
"What is a Response Factor?" Chromatography Today, Aug. 8, 2014, 3 pages.
Fischer et al, "A Novel Approach to Enzymatic Peptide Synthesis Using Highly Solubilizing Na-Protecting Groups of Amino Acids." Biocatalysis 1994, 8:289-307.
International Search Report and Written Opinion for PCT/IB2016/052417 dated Sep. 21, 2016, 11 pages.
Klemes; et al., "Potent and prolonged melanotropic activities of the alpha-MSH fragment analog, Ac-[NIe4,D-Phe7]-alpha-MSH4-9-NH2." Biochem Biophys Res Commun. Jun. 13, 1986; 137(2):722-8.
Suli-Vargha; et al., "The effect of N-terminal substitutions on the biological activity of MSH fragments." Peptides. Nov.-Dec. 1992; 13(6):1145-8.
Suzuki; et al. "Binding of melanotropic hormones to the MC1 receptor on human melanocytes stimulates proliferation and melanogenesis". Endocrinology 137: 1627-1633, 1996.

* cited by examiner

*Primary Examiner* — Sudhakar Katakam
*Assistant Examiner* — Zachary J Miknis
(74) *Attorney, Agent, or Firm* — Casimir Jones, S.C.; Lisa Mueller

(57) ABSTRACT

The present invention relates to compounds comprising a quaternary ammonium group, their use in skin diseases, and their preparation.

11 Claims, No Drawings
Specification includes a Sequence Listing.

PHARMACEUTICAL COMPOUND

CROSS REFERENCE TO RELATED APPLICATIONS

This application is a divisional of U.S. patent application Ser. No. 15/569,586, filed on Oct. 26, 2017, which is a U.S. national stage entry of International Patent Application No. PCT/IB2016/052417, filed on Apr. 28, 2016, which claims priority to European Patent Application No. 15165536.2, filed on Apr. 28, 2015, the entire contents of all of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 905 Byte ASCII (Text) file named "36276-402_ST25.TXT," created on Jul. 27, 2021.

TECHNICAL FIELD

The present invention relates to specific alpha-MSH analogue compounds, a compound for use, use of a compound for manufacturing, a method of preparing a compound, a method of preparing an amino acid or peptide derivative, and a method of treating a subject by therapy.

BACKGROUND TO THE INVENTION

Melanocortins include a family of peptide hormones that induce pigmentation by interaction with the melanocortin-1-Receptor (MC1R) in the epidermis. Alpha-melanocyte stimulating hormone (alpha-MSH) is a primary pigmentary hormone that is released from the pars *intermedia* of the pituitary gland in some non-human animals, and from UV exposed keratinocytes in human skin. This 13 amino acid peptide is represented by the formula structure Ac-Ser-Tyr-Ser-Met-Glu-His-Phe-Arg-Trp-Gly-Lys-Pro-Val-NH$_2$ (SEQ ID NO: 1). Alpha-MSH binds to MC1R and induces cyclic AMP-mediated signal transduction leading to the synthesis of melanin polymers from DOPA precursors. Various alpha-MSH analogues have been described in WO2008025094 and WO2012107592.

Two types of melanin can be expressed in humans, melanin and phaeomelanin. The brownish-black pigment melanin is believed to have photoprotective properties as it is resistant to photodegradation and has the ability to quench reactive oxygen radicals. Phaeomelanin is a reddish, sulfur-containing pigment and is often expressed in light-skinned human subjects that report a poor tanning response to sunlight and are generally thought to be at a greater risk of developing both melanoma and non-melanoma skin cancers. Binding of alpha-MSH to MC1R further stimulates eumelanogenesis through activation of adenylate cyclas.

While advances have been made in treating skin and other diseases, there remains a need for more and/or improved options in the art for compounds and medical treatments.

SUMMARY OF THE INVENTION

According to one aspect of the invention, we have surprisingly found that modifications, such as introduction of a quaternary ammonium group (a quaternary, positively charged nitrogen atom with four substituents) in the backbone of an alpha-MSH analogue are associated with benefits, including increased efficacy and/or efficient preparation, with high yield and/or high purity.

In one aspect of the invention, the alpha-MSH analogue compound is a derivative of alpha-MSH which exhibits agonist activity for the melanocortin-1 receptor (MC1R), the receptor to which alpha-MSH binds to initiate the production of melanin within a melanocyte, wherein the alpha-MSH analogue comprises a quaternary ammonium group in the backbone.

In an aspect of the invention, the quaternary ammonium group (that is attached to the alpha-MSH analogue) has three substituents independently selected from methyl, ethyl and propyl. Preferably, the positively charged ammonium group is attached to the backbone of the alpha-MSH analogue with a —(CH$_2$)$_n$—CO— intermediate group wherein n=1-4, preferably 1-3 and more preferably 1 or 3. For the purpose of the invention, the —(CH$_2$)$_n$—CO— intermediate group is part of the quaternary ammonium group.

In a further aspect of the invention, the alpha-MSH analogue (that is attached to the quaternary ammonium group) is preferably a hexapeptide providing added benefits to the compound of the invention, including lower production effort and/or costs, less susceptible to degradation, increased activity and increased potency, particularly on a per weight basis. Preferably, the hexapeptide comprises the following 6 units: Nle-Glu-His-D-Phe-X-Trp-NH$_2$ (SEQ ID NO: 2) wherein X is selected from Arg, HomoArg and/or NorArg, preferably Arg or homoArg, providing the compound with added benefits including increased efficacy and efficient preparation, with high yield and/or high purity. Selection of homoArg provides further preferred benefits, including less susceptibility to degradation, increased efficacy, more stability and a high-yield preparation method.

Accordingly, the invention relates to an alpha-MSH analogue compound that is a derivative of alpha-MSH which exhibits agonist activity for the melanocortin-1 receptor (MC1R), the receptor to which alpha-MSH binds to initiate the production of melanin within a melanocyte, wherein the alpha-MSH analogue comprises a quaternary ammonium group in the backbone.

The invention further relates to a compound with formula structure:

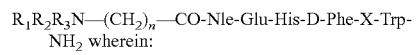

R$_1$R$_2$R$_3$N—(CH$_2$)$_n$—CO-Nle-Glu-His-D-Phe-X-Trp-NH$_2$ wherein:

R$_1$, R$_2$ and R$_3$ are independently selected from methyl, ethyl, and propyl;
n is from 1-4; and
X is selected from Arg, norArg and homoArg,
or a pharmaceutically acceptable salt thereof.

A preferred compound (compound 1) is (C$_2$H$_5$)$_3$N—CH$_2$—CO-Nle-Glu-His-D-Phe-Arg-Trp-NH$_2$ or a pharmaceutically acceptable salt thereof.

A preferred compound (compound 2) is (CH$_3$)$_3$N—(CH$_2$)$_3$—CO-Nle-Glu-His-D-Phe-Arg-Trp-NH$_2$ or a pharmaceutically acceptable salt thereof.

A preferred compound (compound 3) is (C$_2$H$_5$)$_3$N—CH$_2$—CO-Nle-Glu-His-D-Phe-homoArg-Trp-NH$_2$ or a pharmaceutically acceptable salt thereof.

A preferred compound (compound 4) is (CH$_3$)$_3$N—(CH$_2$)$_3$—CO-Nle-Glu-His-D-Phe-homoArg-Trp-NH$_2$ or a pharmaceutically acceptable salt thereof.

A preferred compound (compound 5) is (C$_2$H$_5$)$_3$N—CH$_2$—CO-Nle-Glu-His-D-Phe-norArg-Trp-NH$_2$ or a pharmaceutically acceptable salt thereof.

A preferred compound (compound 6) is (CH$_3$)$_3$N—(CH$_2$)$_3$—CO-Nle-Glu-His-D-Phe-norArg-Trp-NH$_2$ or a pharmaceutically acceptable salt thereof.

In a further embodiment, the compound of the invention is for use as a medicine. Preferably, the compound of the invention is for use in therapeutic treatment of a skin disorder. Preferably, the compound is for use in treating pigmentation disorders, photodermatoses, prevention of skin cancer, and/or DNA repair in skin cells. Preferably, the compound is applied topically to the skin or via a sustained or extended release formulation.

In a further embodiment, the invention relates to use of a compound according for the manufacture of a medicine. The compound is preferably included in a pharmaceutically active product for medicinal use.

In a further embodiment, the invention relates to a method of preparing compound R$_1$R$_2$R$_3$N—(CH$_2$)$_n$—CO-Nle-Glu-His-D-Phe-X-Trp-NH$_2$, or a pharmaceutically acceptable salt thereof, wherein R$_1$, R$_2$ and R$_3$ are independently selected from methyl, ethyl, and propyl;
n is from 1-4; and
X is selected from Arg, norArg and/or homoArg, by
  providing tripeptide D-Phe-X-Trp (4-6);
  coupling the tripeptide (4-6) D-Phe-X-Trp with histidine (3);
  coupling quaternary ammonium compound R$_1$R$_2$R$_3$N$^+$—(CH$_2$)$_n$—COO$^-$ with the dipeptide Nle-Glu (1-2); and
  coupling the dipeptide Nle-Glu (1-2) carrying the quaternary ammonium group with the tetrapeptide His-D-Phe-X-Trp (3-6) to prepare the compound R$_1$R$_2$R$_3$N—(CH$_2$)$_n$—CO-Nle-Glu-His-D-Phe-X-Trp-NH$_2$.

A preferred method of this method wherein X is homoArg is to prepare tripeptide D-Phe-homoArg-Trp (4-6) from tripeptide D-Phe-Lys-Trp by converting the free amino function of the Lysine side chain with guanylating reagent benzotriazole-1-carboxamidinium tosylate (BCAT). Optionally, the Lys group is temporarily protected and conversion of Lys to homoArg takes place in a later step in the preparation method of the alpha-MSH analogue compound.

In a further embodiment, the invention relates to a method of preparing an amino acid or peptide derivative comprising a quaternary ammonium group R$_1$R$_2$R$_3$N$^+$—(CH$_2$)$_n$—CO— wherein
R$_1$, R$_2$ and R$_3$ are independently selected from methyl, ethyl and propyl; and
n is from 1-4,
using the acid chloride of quaternary ammonium compound R$_1$R$_2$R$_3$N$^+$—(CH$_2$)$_n$—COO$^-$ and an amino acid based compound comprising a persilylated group, by reacting the acid chloride of quaternary ammonium compound with the persilylated group of the amino acid based compound.

In a further embodiment, the invention relates to a method of treating a subject by therapy by administering a compound with formula structure:

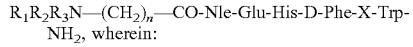
R$_1$R$_2$R$_3$N—(CH$_2$)$_n$—CO-Nle-Glu-His-D-Phe-X-Trp-NH$_2$, wherein:

R$_1$, R$_2$ and R$_3$ are independently selected from methyl, ethyl, and propyl;
n is from 1-4; and
X is selected from Arg, norArg and homoArg,
or a pharmaceutically acceptable salt thereof.

We have surprisingly found that compounds of the present invention provide beneficial results in in-vitro and/or in-vivo tests for instance relating to MC1R binding affinity, potency, and/or efficacy or showing increased stability, and are in particular useful for increasing MC1R expression as a medicinal target. Further, we have found that compounds of the invention can safely and efficiently be synthesized, particularly at high yield.

DETAILED DESCRIPTION OF THE INVENTION

For the purpose of the invention, the term "alpha-MSH analogue" referred to herein is defined as a derivative of alpha-MSH which exhibits agonist activity for the melanocortin-1 receptor (MC1R), the receptor to which alpha-MSH binds to initiate the production of melanin within a melanocyte.

The following abbreviations have been used in this specification: Arg—arginine, D-Phe—D isomer of Phenylalanine; Glu—Glutamic acid; Gly—Glycine; His—Histidine; HomoArg—homoarginine (one additional —CH$_2$— unit in the alkyl chain compared to Arg); Lys—Lysine; Met—Methionine; Nle—Norleucine; NorArg—Norarginine (one less —CH$_2$— unit in the alkyl chain than Arg); Phe-Phenylalanine; Ser—Serine; Trp—Tryptophan. The prefix "D" before the amino acid designates the D-isomer configuration. Unless specifically designated otherwise, all amino acids are in the L-isomer configuration.

All peptide and peptide derivatives are written with the acylated amino terminal end at the left and—at the opposite end of the linear configured molecule—the amidated carboxyl terminal at the right. As will be understood, the acylated amino terminal end may be replaced by another group according to the invention but the orientation of the peptides and peptide derivatives remains the same. Following common convention, the first amino acid on the left is located at position 1, for instance, Nle (1) indicating that Nle is positioned at the N terminal end (on the left).

In this specification, homoArg and norArg may be referred to as amino acids even though they are strictly amino acid derivatives. In the same way, compounds comprising quaternary ammonium groups, homoArg, norArg and/or other amino acid derivatives may be referred to as peptides even though they are strictly peptide derivatives. Accordingly, the skilled person will understand that reference in this document to peptide molecules (including hexapeptides and alpha-MSH analogues) includes reference to derivatives thereof.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention relates to alpha-MSH analogues comprising a quaternary ammonium group, preferably as part of the backbone of the alpha-MSH analogue wherein the alpha-MSH derivative is preferably a hexapeptide, more preferably a hexapeptide comprising the following 6 amino acids: -Nle-Glu-His-D-Phe-X-Trp-NH$_2$ (SEQ ID NO: 2) wherein X is Arg, HomoArg or NorArg. According to one aspect of the invention, Arg is replaced by NorArg or preferably HomoArg in the backbone of the alpha-MSH analogue for added benefits, including increased efficacy.

According to the invention, the compounds preferably have a quaternary ammonium group. The quaternary ammonium group is preferably part of the backbone of the alpha-MSH analogue and is preferably attached to the end of the backbone, most preferably to the amino acid unit in position 1 of the peptide (on the left side, using the representation of the convention used herein), preferably replacing the Ac unit, and preferably being attached to a Nle-unit as the amino acid in position 1 of the peptide. In addition to being attached to the alpha-MSH analogue backbone, the quaternary ammonium group preferably comprises 3 substituent groups $R_1$, $R_2$ and $R_3$ that are each independently selected from methyl, ethyl and propyl, preferably methyl and ethyl. Preferably, the quaternary ammonium group further comprises group $R_4$ represented by intermediate group —$(CH_2)_n$—CO— wherein n is from 1-4, preferably n is from 1 to 3, more preferably 1 or 3. Preferably, the intermediate group $R_4$ of the quaternary ammonium group is attached to the backbone of the alpha-MSH analogue, preferably to Nle unit at position 1 in the backbone.

A preferred quaternary ammonium group is $Et_3NCH_2CO$— group, which is called a triethylglycyl group and which may be written as $(C_2H_5)_3N$—$CH_2$— CO—. Another preferred quaternary ammonium group is $Me_3N$—$CH_2$—$CH_2$—$CH_2$—CO— group, which is called a butyrobeta'inyl group and which may be written as $(CH_3)_3N$—$(CH_2)_3$— CO—. Thus, according to the invention, the quaternary ammonium group is preferably selected from triethylglycyl and butyrobeta'inyl.

The alpha-MSH analogue preferably comprises a group selected from Arg, homoArg and norArg. Preferably, the alpha-MSH compound is a hexapeptide. Preferably, the backbone of the hexapeptide comprises the following 6 amino acids: -Nle-Glu-His-D-Phe-X-Trp-$NH_2$ (SEQ ID NO: 2) wherein X is Arg, homoArg or norArg and wherein -Nle is attached to the quaternary ammonium group. According to one aspect of the invention, Arg is replaced by NorArg or preferably HomoArg in the backbone of the alpha-MSH analogue for added benefits, including increased efficacy.

The preferred MC1R agonist alpha-MSH analogue molecule can be represented as: $R_1R_2R_3N^+$— $R_4$—$R_5$, wherein $R_4$ represents —$(CH_2)_n$—CO— and $R_5$ represents the alpha-MSH analogue which is preferably -Nle-Glu-His-D-Phe-X-Trp-$NH_2$ (SEQ ID NO: 2), wherein X is selected from Arg, homoArg and/or norArg. An MC1R agonist alpha-MSH analogue molecule is defined as a derivative of alpha-MSH with agonist activity on the MC1R, the receptor to which alpha-MSH binds to initiate the production of melanin within a melanocyte.

In one aspect, the present invention relates to $(C_2H_5)_3N$—$CH_2$— CO-Nle-Glu-His-D-Phe-Arg-Trp-$NH_2$ or a pharmaceutically acceptable salt thereof. In another aspect, the present invention relates to $(CH_3)_3N$—$(CH_2)_3$—CO-Nle-Glu-His-D-Phe-Arg-Trp-$NH_2$ or a pharmaceutically acceptable salt thereof. In another aspect, the present invention relates to $(C_2H_5)_3N$—$CH_2$—CO-Nle-Glu-His-D-Phe-homoArg-Trp-$NH_2$ or a pharmaceutically acceptable salt thereof. In another aspect, the present invention relates to $(CH_3)_3N$—$(CH_2)_3$—CO-Nle-Glu-His-D-Phe-homoArg-Trp-$NH_2$ or a pharmaceutically acceptable salt thereof. In another aspect, the present invention relates to $(C_2H_5)_3N$—$CH_2$—CO-Nle-Glu-His-D-Phe-norArg-Trp-$NH_2$ or a pharmaceutically acceptable salt thereof. In another aspect, the present invention relates to $(CH_3)_3N$—$(CH_2)_3$—CO-Nle-Glu-His-D-Phe-norArg-Trp-$NH_2$ or a pharmaceutically acceptable salt thereof.

Preferably, the quaternary ammonium group confers a positive charge to the compound of the invention, which is—according to convention—represented with a plus sign next to the Nitrogen atom, i.e. N. Also, depending on the environment, certain amino acids may act as a base and attract a proton, resulting in a charged in the peptide, as is well known in the art. According to an aspect, the compound is positively charged and is preferably combined with a pharmaceutically acceptable negatively charged counter-ion. Preferably, the counter-ion is a negatively charged pharmaceutically acceptable anion $Y^-$. It will be understood that $Y^-$ can also have a multiple negative charge in which case it is combined with multiple positive $N^+$ cat-ions in one or more compounds of the invention; the compounds of the invention can in principle also have multiple quaternary ammonium groups or other charged groups. Examples of pharmaceutically acceptable anion r are derived from an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid. Optionally, these compounds are halogenated, such as for instance tri-fluoroacetate. Preferably, r is acetate, chloride or sulfate and more preferably acetate.

Synthesis of the preferred compounds is provided below, also generally indicating how to attach quaternary ammonium groups to alpha-MSH analogues according to the invention.

The compounds of the present invention are preferably used as pharmaceutically active agent for medicinal use, as medicine. It will be understood that medical indications of the invention are of a therapeutic nature. For the purpose of the invention, prevention of a disease is considered to be covered by the term treatment.

Compounds of the invention may be beneficially used for treatment and/or prevention of various medical indications, preferably medical indications of an exclusive therapeutic nature. Preferably, reference to the use of the compound of the invention includes not only pharmaceutically acceptable salts, but preferably also the use of prodrugs, stereoisomers, tautomers, hydrates, hydrides and/or solvates of the compounds of the invention.

Compounds of the invention can be used in the manufacture of medicines for treatment of the indications and administrations indicated in this specification.

Preferably, compounds of the invention are used for treatment of diseases wherein the compounds—through association—beneficially increase MC1R expression, as a drug target for the diseases. Examples of such diseases are pigmentation disorders, photodermatoses, prevention of skin cancer, and/or DNA repair in skin cells (after/due to UV exposure). It will most certainly be understood by the skilled person that the disclosure of this specification includes the use of each specific compound of the present invention for each specific of the indications mentioned.

In one aspect, compounds of the invention are used for treatment of pigmentation (or skin pigmentation) disorders. Such disorder can either be hyperpigmentation but in this case particularly hypopigmentation disorders are important. We have found that compounds of the invention can induce melanogenesis and are useful for inducing therapeutic melanogenesis.

In an aspect, the invention relates to inducing melanogenesis in the skin as a treatment for pigmentation disorders with a compound according to the invention. The term "melanogenesis" as used herein is defined as the ability of a subject to produce melanin by melanin-producing cells called melanocytes, for therapeutic purposes. Examples of producing therapeutic melanogenesis are protecting the skin from UV irradiation damage, for instance preventing the skin from developing wrinkles, sun burns and/or cancer.

An important preferred example of a hypopigmentation disorder is vitiligo. Vitiligo is a chronic skin condition that is characterized by loss of pigment, including melanin, resulting in irregular pale, de-pigmented skin that has a different color and aspect than and contrast with the surrounding non-affected, pigmented, darker colored skin tissue. In an aspect, the present invention is directed to treatment of vitiligo, in particular in combination with UV light treatment. Compounds of the invention are preferred for use in the treatment of vitiligo, particularly for repigmentation of vitiliginous lesions and therefore reducing the contrast between the vitiliginous and the surrounding skin tissue.

Photodermatoses are skin diseases that are associated with photosensitivity of the skin to UV irradiation and may be classified into 5 general categories: idiopathic photodermatoses (including polymorphic light eruption (PLE), actinic pruigo, hydroa vacciniforme, chronic actinic dermatitis, and solar urticarial-SU); photodermatoses that are secondary to exogenous agents (including phototoxic and photoallergic reactions); photodermatoses secondary to endogenous agents (mainly the porphyrias including Erythropoietic PhotoPorphyria-EPP); photoexacerbated dermatoses (including autoimmune disease, infectious conditions, and nutritional deficiencies); and genodermatoses.

In an aspect, the present invention is directed to treatment of photodermatoses. Compounds of the present invention are preferred for use in treatment of photodermatoses, particularly for EPP, PLE, and SU, most particularly for EPP.

Skin cancer includes melanoma and non-melanoma cancer. Generally, higher skin melanin levels are considered a measure for prevention of skin cancer. In an aspect, the present invention is directed using the compounds of the invention for prevention of cancer. Compounds of the invention are preferred for use in the prevention of cancer, particularly skin cancer including melanoma and particularly non-melanoma. While the general public will benefit from skin cancer prevention through the invention, certain patient groups will in particular benefit from the use of compounds of the invention, including immunocompromised patients (particularly HIV-AIDS patients, allogeneic transplant patients, i.e. the recipient receives the transplant from another subject, and/or patients on immunosuppressant medication), human subjects having one or more MC1R variant alleles associated with loss of or diminished receptor function (preferably selected from Val60LEU (V60L), Asp84Glu (D84E), Val92Met (V92M), Arg142His (R142H), Arg151Cys (R151C), Arg160Trp (R160W) and Asp294His (D294H)).

It is understood that UV irradiation can cause damage to DNA, particularly the DNA of dermal (skin) cells. In an aspect, the present invention is direct to DNA repair. Accordingly, the present invention is directed to compounds of the invention for use in DNA repair, preferably in the skin, particularly subsequent to UV irradiation of the skin.

Preferably, the compound of the invention is used on subject wherein the subject preferably being a mammal, preferably rodents and/or humans, more preferably a human subject.

In one aspect of the invention, the compound of the invention is combined with UV light for treatment of the subject.

Any of the compounds useful herein can be administered to a subject using a variety of administration or delivery techniques known in the art. The mode of administration will depend upon the subject to be treated and compound selected. In various aspects, the compound can be administered orally (or enterally), parenterally or topically (preferably to the skin).

The term "oral" is used herein to encompass administration of the compounds via the digestive tract.

The term "parenteral" is used herein to encompass any route of administration, other than oral administration, by which the compound is introduced into the systemic circulation. Generally, parenteral administration can be achieved by intravenous, intramuscular, subcutaneous, intraperitoneal, intradermal, ocular, inhalable, nasal, rectal, vaginal, transdermal, buccal, sublingual, or mucosal administration.

The term "mucosal" as used herein encompasses the administration of the compounds by methods that employ the mucosa (mucous membranes) of the subject's body such as, but not limited to, buccal, intranasal, gingival, vaginal, sublingual, pulmonary, or rectal tissue.

The term "transdermal" as used herein encompasses the administration of the compounds that are applied to the skin and subsequently pass through the skin into the systemic circulation such as, but not limited to, transdermal formulations, buccal patches, skin patches, or transdermal patches.

The term "topical" as used herein encompasses administration to the skin and may include applying preparations such as creams, gels, or solutions to the skin, eye, or mucosal areas for local effect. Compounds of the invention may be incorporated into a topical composition for administered on the skin. In one aspect, the topical compositions has local efficacy in the skin at the location of application and is thus administered locally. In another aspect, the topical composition has systemic efficacy which requires the compound migrate transdermally (through the skin) into the blood stream resulting in systemic exposure to the compound and is thus administered transdermally.

Other preferred administration routes that may achieve systemic exposure to the compounds are subcutaneous ("under the skin") and intramuscular ("in the muscle").

In one aspect, the compound of the invention is topically administered to the skin. Accordingly, the invention relates to administering the compound of the invention to the skin of a subject. In another aspect, the compound of the invention is parentally administered to the skin. Accordingly, the invention relates to administering the compound of the invention through the skin of a subject.

Preferably, the compounds of the invention are formulated in a composition. The composition is preferably a pharmaceutical composition. The composition preferably comprises at least one pharmaceutically-acceptable ingredient in addition to the compounds of the invention. Examples of such pharmaceutically-acceptable ingredients are carriers, polymers, thickeners, diluents, fillers, buffers, preservatives, and surface active agents.

In an aspect, the composition is a sustained or controlled release formulation, resulting in longer and/or more controlled exposure of the body to the compound. The composition may be an implant. In one preferred embodiment, the compound is administered in a prolonged release implant formulation such as described in WO2006/012667.

Preparation Process

Compounds of the invention are preferably prepared as follows, though the skilled person will appreciate reviewing this specification that alterations of the presented methods could be employed that are also covered by the presently claimed invention. According to a preferred method, compounds of the invention are prepared by liquid phase or solid phase peptide synthesis, preferably followed by chromatographic purification and preferably by lyophilisation.

Generally, the present invention relates to preparation of alpha MSH analogue compound

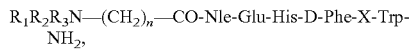

or a pharmaceutically acceptable salt thereof,
wherein
$R_1$, $R_2$ and $R_3$ are independently selected from methyl, ethyl, and propyl;
n is from 1-4; and
X is selected from Arg, homoArg or norArg, by
step 1: providing tripeptide D-Phe-X-Trp (4-6);
step 2: coupling the tripeptide (4-6) D-Phe-X-Trp with histidine (3);
step 3: coupling quaternary ammonium compound $R_1R_2R_3N^+$—$(CH_2)_n$—$COO^-$ with the dipeptide Nle-Glu (1-2); and
step 4: coupling the dipeptide Nle-Glu (1-2) carrying the quaternary ammonium group with the tetrapeptide His-D-Phe-X-Trp (3-6) to prepare the compound $R_1R_2R_3N$—$(CH_2)_n$—CO-Nle-Glu-His-D-Phe-X-Trp-$NH_2$.

Preferably, the compound is purified (step 5); preferably, the compound is concentrated (step 6); and preferably, the compound is lyophilized (step 7).

Specifically, synthesis steps of the compounds of the invention comprising -Nle-Glu-His-D-Phe-X-Trp, (representing $R_5$ of the formula structure), wherein X is Arg or homoArg, include the following steps in more detail:

Step 1: Deprotection of tripeptide D-Phe-X-Trp (4-6) by hydrogenolysis with a Pd/C catalyst in ethanol;
Step 2a: Deprotected tripeptide (4-6) coupling to (Fmoc) and (Trt) protected histidine (3) with HBTU/DIPEA in a dichloromethane dimethylformamide mixture;
Step 2b: Detritylation of the protected (3-6) peptide in a HOAc/H2O mixture;
Step 2c: Cleavage of the Fmoc protective group of the (3-6) peptide in a mixture of H20/methanol and dioxane with NaOH;
Step 3: coupling quaternary ammonium compound $R_1R_2R_3N^+$—$(CH_2)_n$—$COO^-$ with the dipeptide based compound Nle-Glu(Ot.Bu);
Step 4: Coupling of the (1-2) dipeptide Nle-Glu(Ot.Bu) already carrying the quaternary ammonium group to the (3-6) peptide with DCC/HOOBt in dimethylformamide.
Step 4a: Removal of the Ot.Bu protective group from the side chain of residue 2 (Glu) by treatment with 8NHCl and phenol;
Step 5. Purification of the peptides by preparative RP-HPLC using a C-18 column and a purified water/acetonitrile/TFA eluent;
Step 6. Concentration step using the same chromatographic column with an eluent composed of the same components but with higher acetonitrile content. Organic solvents are removed by evaporation;
Step 7: Lyophilization of the aqueous solution obtained after evaporation of the organic solvents.

Each of these more specific synthesis steps can independently be introduced to the above general preparation method, arriving at a preferred process. Thus, each preferred step separately represents preferred conditions for the preparation of the compound of the invention.

In a preferred aspect, as will be further explained below, introduction of the homoArg group preferably occurs by first incorporating Lys and converting Lys into homoArg. Optionally, conversion of Lys to homoArg takes place in a later step of the preparation, requiring temporary protection of the Lys group, for instance with a trifluoro acetyl group.

The abbreviations used herein will be readily understood by the skilled person, the following list only being provided for convenience:
Ac: acetyl or $CH_3$—CO—
BCAT: benzotriazole-1-carboxamidinium tosylate
DCC: dicyclohexylcarbidiimide
DIPEA: diisopropylethylamine
Et3NCH2CO— group: triethylglycyl group
Fmoc: fluorenylmethoxycarbonyl
HBTU: benzotriazolyl tetramethyluronium hexafluorophosphate
HOOBT: 3-hydroxy-3,4dihydro-4oxo-benzotriazine
Me3N—CH2-CH2-CH2-CO— group: butyrobeta'inyl group
OtBu- group: 0-tert-butyl group
Trt- group: trityl group
TMS: trimethylsilyl Process of Coupling the Quaternary Ammonium Group Surprisingly, we have found that the quaternary ammonium group can be beneficially introduced in alpha-MSH analogues, using easy processing conditions and resulting in high yields. Such process allows for attachment to the alpha-MSH analogues of WO2008025094, which formula structures are incorporated herein by reference for purpose of defining the process. The preferred process for attaching the quaternary ammonium group to the alpha-MSH analogue is indicated below.

Preferably the persilylated group is attached to the amino acid at position 1 of the alpha-MSH analogue (the right terminal end; the side where it replaces the Ac group), which is preferably a Nle group. The reaction process replaces the persilylated group on the alpha-MSH analogue with the quaternary ammonium group.

In a further embodiment, the invention relates to a method of preparing an amino acid or peptide connected to a quaternary ammonium group $R_1R_2R_3N^+$—$(CH_2)_n$—CO— wherein
$R_1$, $R_2$ and $R_3$ are independently selected from methyl, ethyl and propyl; and
n is from 1-4,
using the acid chloride of quaternary ammonium compound $R_1R_2R_3N^+$—$(CH_2)_n$—$COO^-$ and an amino acid based compound comprising a persilylated group, by
(step a:) reacting the acid chloride of quaternary ammonium compound with the persilylated group of the amino acid based compound.

Preferably, the amino acid based compound is an amino acid or a peptide. Preferably, the amino acid based compound comprises Nle as end group, more preferably the amino acid based compound is dipeptide Nle-Glu and most preferably the persilylated 1-2 dipeptide TMS-Nle-Glu(Ot.Bu)-OTMS. Preferably, the acid chloride of quaternary ammonium compound $R_1R_2R_3N^+$—$(CH_2)_n$—$COO^-$ is reacted with TMS-Nle-Glu(Ot.Bu)-OTMS.

Preferably, the quaternary ammonium coupling process is used for the preparation of the alpha-MSH analogue as defined above, more preferably, the quaternary ammonium group is attached to the hexapeptide Nle-Glu-His-D-Phe-X-Trp-$NH_2$ (SEQ ID NO: 2) wherein X is selected from Arg, norArg and homoArg, and other preferred specific compounds identified above. Preferably, this process is used in step 3 of the process mentioned above.

Preferably, step a takes place in solvent, which is preferably acetonitrile. Preferably, an excess of the acid chloride is used in step a. Preferably, step a is followed by step b: desilylating the analogue. Preferably, step b occurs in solvent which is preferably water saturated ethylacetate. Preferably, the excess acid chloride is destroyed in step b. Preferably step a and/or b is followed by step c: the excess precipitate is filtered off. Preferably, subsequent step d is used: the filtrate is concentrated by evaporation. Preferably, subsequent step e is used: the residue is triturated with solvent which is preferably dimethoxyethane.

Preferred quaternary ammonium compounds —as indicated above—are $R_1R_2R_3N^+$—$(CH_2)_n$—$COO^-$ wherein:
$R_1, R_2$ and $R_3$ are independently selected from methyl, ethyl, and propyl; and
n is from 1-4.

The acid chloride of these quaternary ammonium compounds would be preferred for use in this process. Particularly preferred quaternary ammonium compounds are triethylglycine and butyrobetaine. The acid chlorides thereof are preferred in the above process of the invention.

Process of Introducing the homoArg Unit in the Compound

The compound of the invention may comprise a homoArg unit. The homoArg unit can be introduced as a homoArg unit in the tripeptide of above mentioned step 1.

Surprisingly, we have found that the homoArg amino acid derivative can be beneficially introduced in the peptide derivate of the invention, using easy and efficient processing conditions and resulting in high yields for reduced expenses.

Accordingly, the present invention relates to a process of preparing an alpha-MSH analogue, preferably a compound of the present invention, comprising a homoArg group by first preparing D-Phe-Lys-Trp and subsequently converting the Lys group to a homoArg group by reaction of the free amino function of the Lysine side chain with guanylating reagent benzotriazole-1-carboxamidinium tosylate (BCAT). Instead of directly synthesizing the D-Phe-homoArg-Trp, we have found that first introducing a Lysine group and then converting the Lysine group to homoArg leads to reduced expenses with good yields.

Preferably, the Lysine group is introduced and converted to homoArg before above-mentioned step 1. Optionally, the Lysine group may be introduced before above mentioned step 1 but converted to homoArg in a later step in the preparation of the compound of the invention. In that case, the free amino function of the Lysine group is preferably temporarily protected. Protection can for instance be carried out with a trifluoro acetyl group. In the later step and after de-protecting, Lys is converted to homoArg with guanylating reagent benzotriazole-1-carboxamidinium tosylate (BCAT).

EXAMPLES

The following examples are illustrative to the present invention and are presented without wishing to limit the scope of the present invention to the specific examples.

Example 1: Coupling Quaternary Ammonium Compound to Dipeptide

Excess of the acid chloride of the triethylglycine or butyrobetaine is coupled to the persilylated 1-2 dipeptide TMS-Nle-Glu(Ot.Bu)-OTMS in acetonitrile. Once the reaction has completed, the excess of the acid chloride is destroyed and the dipeptide de-silylated by the addition of water saturated ethylacetate. The excess of triethylglycine or butyrobetaine which precipitates is filtered off, the filtrate concentrated by evaporation and the residue triturated with dimethoxyethane. The yield was 70%.

Example 2: Preparation and Characterization of Compounds 1, 2, 3 and 4

Compounds 1 and 2 of the present invention were prepared using the above mentioned processing steps 1-7. In step 3 of the coupling to the [3-6] hexapeptide, the N-unprotected 1-2 dipeptide (Nle-Glu(OtBu)) was reacted with the acid chloride of respectively triethylglycine and butyrobetaine following above-mentioned steps a, b, c, d and e with the preferred solvents. Following these steps resulted for compound 1 in the triethylglycyl group (Et3NCH2CO—) being attached to the amino acid in position 1 (Norleucine) and for compound 2 in the butyrobeta'inyl group ($Me_3N$—CH2-CH2-CH2-CO—) being attached to the amino acid in position 1 (Norleucine).

Compounds 3 and 4 of the present invention were generally prepared using the above synthesis steps of compounds 1 and 2 including the incorporation of triethylglycine and butyrobetaine respectively but with the modification that the amino acid arginine (5) was replaced by its higher homolog homoarginine as follows: before step 1 of the synthesis, a protected derivative of lysine was incorporated at the level of the tripeptide 4-6, then the lysine tripeptide was partially deprotected and the free amino function of the Lysine side chain was converted to a homoarginine with guanylating reagent benzotriazole-1-carboxamidinium tosylate (BCAT). As a result, both compounds 3 and 4 comprised a homoArg unit. Further, compound 3 had a triethylglycyl group ($Et_3NCH2CO$—) attached to the amino acid in position 1 (Norleucine) while compound 4 had a butyrobeta'inyl group ($Me_3N$—CH2-CH2-CH2-CO) attached to the amino acid in position 1 (Norleucine).

Identify and purity of compounds 1, 2, 3 and 4 were confirmed by MS (not including the trifluoroacetate anion) and HPLC and the following results were obtained:

| Compound | MW by Mass spec | HPLC purity |
| --- | --- | --- |
| 1 | 1026 | 99% |
| 2 | 1012 | 98.9% |
| 3 | 1040 | 99.4% |
| 4 | 1026 | 98.2% |

Proof of identity was further provided with 500 MHz proton spectra.

Example 3: Effects on cAMP

Compounds 1, 2, 3 and 4 were tested in various separate tests and using 2 different human melanocyte cultures, coded 1750 and 1753, that were derived from 2 different donors expressing functional MC1R. The melanocytes were plated at a density of $0.3*10^6$ cells/well. After 48 hours, the melanocytes were treated with the different compound concentrations for 1 hour. Controls without compound were included in all experiments. In some experiments reference compound NDP-MSH was included. The reaction was stopped by addition of 50 μl N HCl and the supernatant in each well was used to measure cAMP using a radioimmunoassay as described by Suzuki 1996 (Suzuki I, Cone R D, Im S, Nordlund ii, Abdel-Malek Z: "Binding of melanotropic hormones to the MC1 receptor on human melanocytes stimulates proliferation and melanogenesis". Endocrinology 137: 1627-1633, 1996). Duplicate samples from each well were assayed with triplicate wells included in each compound group. The results from different tests cannot be compared due to differences in melanocyte cultures and to different passage number. The mean of 6 cAMP measurements per group was expressed as % of the control group. Statistical analysis was carried out using ANOVA followed by Newman Kuels test. In some cases, unpaired t-test was used.

Following are the results comparing the compounds in the test indicated:

Test 1 evaluated compounds 1, 2, and 3 on melanocytes 1750 and measured cAMP.

Compound 2 achieved its maximum effect (vs control) at the lowest dose ($10^{-8}$ M) which was statistically different compared to the control at p<0.05.

Compound 3 showed the highest overall efficacy value (327% at $10^{-7}$M vs control; this was statistically different compared to the control at p<0.05).

Test 2 evaluated compounds 1, 2, and 3 on melanocytes 1753 and measured cAMP.

Compound 1 achieved the highest overall efficacy value (431% at $10^{-7}$M vs control) which was statistically different compared to the control at p<0.05.

Compound 2 already showed efficacy at $10^{-11}$ M (lowest dose of the compounds showing efficacy that was statistically different compared to the control at p<0.05).

Compound 3 achieved its maximum effect at the lowest dose ($10^{-9}$M) which was statistically different compared to the control at p<0.05.

Test 3 evaluated compound 4 and reference NDP-MSH on melanocytes 1753 and cAMP. Compound 4 outperformed reference compound NDP-MSH & achieved highest efficacy (253% at $10^{-7}$M vs 202% at $10^{-7}$M) which was statistically different compared to the control at p<0.05.

It is concluded that compounds 1, 2, 3 and 4 showed excellent efficacy results on the test measuring cAMP, the second messenger of the MC1R response.

Example 4: Effects on Tyrosinase Activity

Compounds 1, 2, 3 and 4 were tested in various separate tests and using 2 different human melanocyte cultures, coded 1750 and 1753, that were derived from 2 different donors expressing functional MC1R. The melanocytes were plated at a density of $0.3*10^6$ cells onto 60 mm dishes (triplicate dishes/group). After 48 hours, the melanocytes were treated every other day for a total of six days with different doses of each compound. Controls without compound were included in all experiments. In some experiments reference compound NDP-MSH was included. On treatment day 5, $^3$H-labeled tyrosine, the substrate for tyrosinase, was added and 24 hours later, the supernatant was saved to be assayed for tyrosinase activity as described by Suzuki et al (see example 3). Duplicate samples from each were assayed, with triplicate dishes included in each group. Cell number in each dish was counted, and tyrosinase activity was expressed as dpm/$10^6$ cells and as % of the control. Tests results between separate tests cannot be compared due to differences in melanocyte cultures and to different passage number. Statistical analysis was carried out using ANOVA followed by Newman Kuels test.

It will be understood that this tyrosinase activation test relates to a late event after MC1R activation, compared to the earlier secondary messenger effect of the above cAMP test. As pointed out above, activity of tyrosinase requires days of treatment. Following are the results comparing the compounds in the test indicated:

Test 4 evaluated compounds 1, 2 and reference NDP-MSH on melanocytes 1750 and measured tyrosinase.

Compounds 1 and 2 both just outperformed reference compound NDP-MSH having higher efficacy (178% vs 171% vs 166%) and were both statistically different compared to the control (at p<0.05) at concentrations from $10^{-10}$ M to $10^{-7}$M.

Test 5 evaluated compounds 3 and 4 on melanocytes 1750 and measured tyrosinase. Compounds 3 and 4 showed similar efficacy which was statistically different compared to the control at p<0.05 at concentrations from $10^{-10}$ M to $10^{-7}$M.

Test 6 evaluated compounds 1, 2, 3 and 4 on melanocytes 1753 and measured tyrosinase. Compounds 1 and 2 showed similar efficacy at the same doses which were statistically different compared to the control (at p<0.05) at concentrations from $10^{-10}$ M to $10^{-7}$M. Compounds 1 and 2 both beat compounds 3 and 4 which also showed similar efficacy at the same doses and were both statistically different compared to the control at p<0.05 at concentrations from $10^{-10}$ M to $10^{-7}$M.

It is concluded that compounds 1, 2, 3 and 4 also showed excellent efficacy on the test measuring tyrosinase, representing a late event following agonist activity on the MC1R.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An alpha-MSH analogue compound that is a derivative of alpha-MSH which exhibits agonist activity for the melanocortin-1 receptor (MC1R), the receptor to which alpha-MSH binds to initiate the production of melanin within a melanocyte, wherein the alpha-MSH analogue comprises a quaternary ammonium group in the backbone, and wherein the alpha-MSH analogues comprises Arg, norArg and/or homoArg.

2. The compound according to claim 1, wherein the alpha-MSH analogue comprises a quaternary ammonium group at the amino terminal end of the backbone.

3. The compound according to claim 1, wherein the quaternary ammonium group
is $R_1R_2R_3N$—$(CH_2)_n$—
wherein:
$R_1$, $R_2$ and $R_3$ are methyl;
n is from 1-4.

4. Compound according to claim 1, wherein the compound is a hexapeptide.

5. The compound according to claim 1, wherein the compound is $(CH_3)_3N$—$(CH_2)_3$—CO-Nle-Glu-His-D-Phe-Arg-Trp-$NH_2$ or a pharmaceutically acceptable salt thereof.

6. A pharmaceutical composition comprising a compound according to claim 1 and at least one pharmaceutically-acceptable ingredient.

7. The compound according to claim 1, wherein the compound has formula structure:

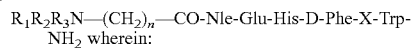

$R_1R_2R_3N$—$(CH_2)_n$—CO-Nle-Glu-His-D-Phe-X-Trp-$NH_2$ wherein:

$R_1$, $R_2$ and $R_3$ are independently selected from methyl, ethyl, and propyl;
n is from 1-4; and
X is selected from Arg, norArg and homoArg,
or a pharmaceutically acceptable salt thereof.

8. The compound according to claim 1, wherein the compound is $(C_2H_5)_3N$—$CH_2$—CO-Nle-Glu-His-D-Phe-homoArg-Trp-$NH_2$ or a pharmaceutically acceptable salt thereof.

9. The compound according to claim 1, wherein the compound is $(CH_3)_3N$—$(CH_2)_3$—CO-Nle-Glu-His-D-Phe-homoArg-Trp-$NH_2$ or a pharmaceutically acceptable salt thereof.

10. The compound according to claim 1, wherein the compound is $(C_2H_5)_3N$—$CH_2$—CO-Nle-Glu-His-D-Phe-norArg-Trp-$NH_2$ or a pharmaceutically acceptable salt thereof.

11. The compound according to claim 1, wherein the compound is $(CH_3)_3N$—$(CH_2)_3$—CO-Nle-Glu-His-D-Phe-norArg-Trp-$NH_2$ or a pharmaceutically acceptable salt thereof.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial sequence
<220> FEATURE:
<223> OTHER INFORMATION: Synthetic

<400> SEQUENCE: 1

Ser Tyr Ser Met Glu His Phe Arg Trp Gly Lys Pro Val
1               5                   10

<210> SEQ ID NO 2
<211> LENGTH: 6
```

```
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is Norleucine
<220> FEATURE:
<221> NAME/KEY: misc_feature
<222> LOCATION: (5)..(5)
<223> OTHER INFORMATION: X is selected from Arginine, Homoarginine and/
      or Norarginine

<400> SEQUENCE: 2

Xaa Glu His Phe Xaa Trp
1               5
```